United States Patent [19]

Hein

[11] Patent Number: 4,612,255

[45] Date of Patent: Sep. 16, 1986

[54] WATER DISPERSIBLE COMPOSITIONS FOR PREPARING AQUEOUS WATER REPELLENT SYSTEMS, AQUEOUS WATER REPELLENT SYSTEMS, AND PROCESS FOR TREATMENT OF PERMEABLE SUBSTRATES THEREWITH

[75] Inventor: Richard W. Hein, Hudson, Ohio

[73] Assignee: Mooney Chemicals, Inc., Cleveland, Ohio

[21] Appl. No.: 682,784

[22] Filed: Dec. 18, 1984

[51] Int. Cl.$^4$ .................. B05D 1/18; C09D 5/16; C09D 5/18

[52] U.S. Cl. .................. 428/541; 106/18.29; 106/18.36; 427/440; 514/494; 514/496; 514/498; 514/499; 514/502; 514/503; 514/505

[58] Field of Search .............. 424/141, 145; 427/440; 106/18.29, 18.36; 428/541; 514/494, 496, 498, 499, 502, 503, 505

[56] References Cited

U.S. PATENT DOCUMENTS

| | | | |
|---|---|---|---|
| 2,668,779 | 2/1954 | Herman | 117/59 |
| 2,951,789 | 9/1960 | McCants | 167/38.5 |
| 3,200,003 | 8/1965 | Bescher | 117/59 |
| 3,244,586 | 4/1966 | Rigterink | 167/33 |
| 3,272,693 | 9/1966 | Harrison | 167/22 |
| 3,677,805 | 7/1972 | Barnett | 117/102 |
| 3,968,276 | 7/1976 | Allen | 427/297 |
| 4,001,400 | 1/1977 | Hager | 424/141 X |
| 4,193,993 | 3/1980 | Hilditch | 424/141 |
| 4,374,852 | 2/1983 | Hilditch et al. | 424/289 |
| 4,388,215 | 6/1983 | Ishida et al. | 252/402 |
| 4,507,152 | 3/1985 | Collins et al. | 106/18.31 |
| 4,532,161 | 7/1985 | Collins et al. | 427/440 |
| 4,539,235 | 9/1985 | Collins et al. | 427/440 |

FOREIGN PATENT DOCUMENTS

| | | |
|---|---|---|
| 5991 | 12/1979 | European Pat. Off. |
| 213590 | 2/1931 | United Kingdom |
| 343891 | 2/1931 | United Kingdom |
| 581083 | 10/1946 | United Kingdom |
| 756685 | 9/1956 | United Kingdom |
| 809708 | 3/1959 | United Kingdom |
| 972198 | 10/1964 | United Kingdom |
| 1069640 | 5/1967 | United Kingdom |
| 1461630 | 1/1977 | United Kingdom |
| 1465214 | 2/1977 | United Kingdom |
| 2049430 | 5/1980 | United Kingdom |
| 1574939 | 9/1980 | United Kingdom |
| 2121285 | 12/1983 | United Kingdom |
| 2126896 | 4/1984 | United Kingdom |

OTHER PUBLICATIONS

Pesticide Manual, Sixth Ed., p. 374, *Naphthenic Acids*.
"The Owl Hoots—Another Big Step for Water Systems—Water-Reducible Copper and Zinc Naphthenate", 6/80.
Technical Sales Release "Copper Hydronap", 8/81, 4 pages, Mooney Chemicals, Inc.
Technical Sales Release "Zinc Hydronap", 8/81, 3 pages, Mooney Chemicals, Inc.

*Primary Examiner*—Michael R. Lusignan
*Attorney, Agent, or Firm*—Renner, Otto, Boisselle & Lyon

[57] ABSTRACT

Water dispersible compositions containing hydrocarbon wax are described which are useful in preparing aqueous water repellent systems. Aqueous water repellent systems containing a hydrocarbon wax also are described. The water repellent system comprises an aqueous system comprising water, a saturated hydrocarbon wax, at least one oil-soluble metal salt of an organic carboxylic acid, at least one surfactant and at least one hydrocarbon solvent. A process for impregnating permeable substrates such as wood, cloth, concrete, rope, etc. with the water repellent system is also described. Penetration of the various components into the substrate is obtained by brushing, dipping, soaking, spraying or immersion at atmospheric pressure, at elevated pressures or under vacuum. The oil-soluble metal salt often is a fungicide. Moreover, additional components can be contained in the aqueous system such as insecticides, colorants, flame retardants, moldicides, wood stabilizing agents, etc.

28 Claims, No Drawings

WATER DISPERSIBLE COMPOSITIONS FOR PREPARING AQUEOUS WATER REPELLENT SYSTEMS, AQUEOUS WATER REPELLENT SYSTEMS, AND PROCESS FOR TREATMENT OF PERMEABLE SUBSTRATES THEREWITH

FIELD OF THE INVENTION

The present invention relates to an aqueous system containing saturated hydrocarbon waxes which can be utilized in the treating of permeable substrates such as wood, cloth, canvas, concrete, rope, etc. More specifically, the present invention relates to an aqueous system containing such waxes and an oil-soluble metal salt of an organic carboxylic acid. The invention also relates to water dispersible compositions useful in preparing said aqueous systems and a process of treating permeable substrates with the aqueous systems of the invention.

In order to prevent decay of wood and timbers, and thereby increase their life, it is common practice to impregnate the wood or timbers with a preservative such as creosote, mixtures of inorganic compounds which are dissolved or dispersed in water, or certain organic compounds which are dissolved in petroleum distillates. The protection afforded by the application of these materials is dependent upon deep and reasonably uniform penetration into the wood or timber by the preservative material.

The subject of wood treatment and wood preservation is discussed in some detail in the two volume treatise entitled "Wood Deterioration and its Prevention by Preservative Treatments", Darrel D. Nicholas, Editor, Syracuse Wood Science Series 5, Syracuse University Press, Syracuse, N.Y., 1973. Among the examples of wood preservatives described therein are various creosote compositions, pentachloro-phenol, copper naphthenate, copper-8-quinolinolate, organotin compounds, organomercury compounds, zinc naphthenate, chlorinated hydrocarbons, ammoniacal copper arsenite (ACA), acid copper chromate (ACC), zinc salts such as zinc chloride, zinc oxide and zinc sulfate, chromated copper arsenate (CCA), etc. In Volume II, Chapter 3, pages 279-298, processes and equipment for treating wood are discussed. The pressure treatment is described as the most effective method of protecting wood against attack of decay, insects, fire, etc. Non-pressure treatments also are discussed in this chapter. Dipping is suggested primarily as a satisfactory surface treatment although some penetration is observed. Another non-pressure technique is the diffusion process with unseasoned wood. The author indicates the process requires long treating periods because of slow diffusion rates.

The use of liquid hydrocarbons for preparing impregnating solutions imparts to the wood strong odors and leaves the wood with a surface which is oily and difficult to paint. Moreover, liquid hydrocarbons are flammable materials requiring special handling and safety precautions which add to the cost of the wood treatment.

Wood treated with organic preservatives dissolved in petroleum distillates have the same disadvantages as wood treated with the hydrocarbons. Using lower boiling petroleum distillates, such as mineral spirits, as the solvent, fails to eliminate the disadvantages completely. Prolonged air seasoning after treatment is frequently required to permit sufficient evaporation of the solvent if the wood is to be painted. During this period of air seasoning, a portion of the preservative can migrate to the surface of the wood with the solvent, and thus, the retention of the preservative in wood is reduced below that contemplated by the treatment.

One technique for utilizing aqueous systems of polyhalophenols is described in U.S. Pat. No. 4,090,000. Briefly, the method involves the use of an aqueous solution containing a water-soluble salt of the polyhalophenol and an acid forming material which can undergo a reaction in the solution to liberate an acid when displaces the polyhalophenol from said salt after the solution is impregnated into the wood.

Regardless of which impregnating solution is employed, the most common commercial procedure for impregnating wood involves subjecting wood to the preservative under relatively high pressures such as 150 to 200 pounds to the square inch for a substantial period of time such as from one hour to 24 hours. The process also may require relatively high temperatures such as from about 75° C. to about 90° to 95° C. Moreover, the application of pressure can cause compression of the outer layers of the wood, particularly after wood is weakened and softened by steaming. The collapse of the wood cells is likely to occur especially when relatively soft, unseasoned wood of low specific gravity is being treated. On collapse of the wood cells in an area, there is formed a relatively impenetrable layer which restricts or even completely blocks the flow of preservatives into the interior of the wood.

It also has been suggested to improve the method of pressure treatment by first subjecting the wood to a vacuum treatment. Examples of prior art patents describing methods of impregnating wood utilizing a vacuum followed by pressure include U.S. Pat. Nos. 2,668,779; 3,200,003 and 3,968,276.

U.S. Pat. No. 3,677,805 describes a modification of the pressure treatment. In this procedure, the wood is immersed in a treatment liquid inside a pressure vessel, and the pressure is increased to operating pressure whereupon the contents of the vessel then are subjected to the action of a pulsating pump which provides sinusoidal pressure pulses within the vessel. In other words, pressure pulses are applied repetitively in modulated amplitude to provide variable pressure peaks above and below the ambient pressure maintained in the pressure vessel. This procedure requires equipment which includes a pulsating pump operating into a pressure vehicle equipped with a pressure release means.

*A Survey Of The Properties Of Commercial Water Repellents And Related Products*, by the United States Department of Agriculture, Forest Service, Forest Products Laboratory, Madison, Wis., November 1945, states that various water repellent systems have been utilized in the past to treat wood. Although on page 20 thereof it is noted that the use of a paraffin wax as a water repellent has been utilized in certain situations in the past, it is with an organic solvent such as mineral spirits. The reference does not teach or suggest any utilization of a paraffin wax in an aqueous system or in connection with an oil-soluble metal salt of an organic carboxylic acid.

The above-described prior art represents a small sampling of the suggestions which have been made for treating wood with water and/or preservative materials to prevent decay. In spite of these many suggestions made in the prior art, there continues to be a need for an inexpensive, safe, non-toxic treatment which is effective and which results in the uniform penetration of the preservative and other chemicals to the core of the wood and which also results in good water repellency.

Water repellent treatments for other types of permeable substrates also are desirable. Considerable effort has been made to develop acceptable treatments for materials such as cloth, canvas, concrete, rope, etc., and a treatment which will be acceptable on all such substrates is especially desirable.

SUMMARY OF THE INVENTION

It is therefore an aspect of this invention to provide water dispersible compositions useful in preparing aqueous water repellent systems.

It is a further aspect of the present invention to provide a water repellent system containing a saturated hydrocarbon wax in an aqueous system.

It is a further aspect of the present invention to provide a wax containing aqueous system which is water repellent, as above, including at least one surfactant and at least one oil-soluble metal salt of an organic carboxylic acid.

It is still another aspect of the present invention to provide a paraffin wax containing aqueous system which is water repellent, as above, which can include additives such as fungicides, insecticides, colorants, moldicides, flame retardants, stabilizers, and the like.

In one embodiment, the water dispersible composition of this invention comprises:
(a) at least one saturated hydrocarbon wax,
(b) at least one metal salt of an organic carboxylic acid,
(c) at least one surfactant, and
(d) at least one hydrocarbon solvent.

Such water dispersible compositions can be mixed or diluted with water to form aqueous water repellent systems. The aqueous systems can be used to treat various permeable substrates in order to render the substrates water repellent and also resistant to insects, fungus, mold, etc.

DESCRIPTION OF THE PREFERRED EMBODIMENTS

In one embodiment, the water dispersible compositions of the present invention comprise:
(a) at least one saturated hydrocarbon wax,
(b) at least one metal salt of an organic carboxylic acid,
(c) at least one surfactant, and
(d) at least one hydrocarbon solvent.

Compositions of the type described above can be considered as concentrates useful in preparing aqueous water-repellent compositions by blending the concentrate with water.

The first component of the water dispersible composition of the present invention is (a) at least one saturated hydrocarbon wax. The wax as utilized in the present invention may be of natural or synthetic origin. Examples of natural waxes include petroleum waxes, and in particular, paraffin waxes. Examples of synthetic waxes which can be utilized in the present invention include certain polymethylene and polyethyene waxes as described more fully below.

The saturated hydrocarbon waxes utilized in the present invention may be characterized by the general formula $C_nH_{2n+2}$ wherein n is from about 18 to about 40. The waxes generally are composed of normal alkanes although isoalkanes and cycloalkanes may be present. Although the saturated hydrocarbon waxes are represented in the above formula as being composed of carbon and hydrogen only, it is contemplated that hydrocarbon waxes containing minor amounts of other elements such as halogen, etc., are within the scope of the present invention. Thus, the term "saturated hydrocarbon" as used in the present invention is intended to include pure hydrocarbons as well as substituted hydrocarbons wherein the extent of substituent does not detract from the hydrocarbon nature of the wax or otherwise affect its utility in the present invention.

The saturated hydrocarbon waxes useful in the present invention also may be characterized by their physical properties. For example, the waxes which are particularly useful in the water dispersible compositions of the present invention are characterized as having a melting point (ASTM D-87) of between about 100° to about 160° F. with the lower temperatures being preferred. Preferably the melting point range is from about 100° to 140° F. Waxes also are characterized by their oil content, and generally, for the purposes of the present invention, the oil content of the wax should be below about 7% by weight and is preferably below about 3% by weight.

The paraffin waxes are particularly preferred as the saturated hydrocarbon wax utilized in the water dispersible compositions of the present invention. Paraffin wax is a petroleum wax composed of about 40-90 weight percent of normal paraffins, and the remainder is $C_{18}$–$C_{36}$ isoalkanes and cycloalkanes. The oil content of paraffin wax is determined by the extent of the refining and finishing processes. Typical physical properties of paraffin waxes which are useful in the water dispersible compositions of the present invention are summarized in the following Table I.

TABLE I

| PARAFFIN WAXES | |
|---|---|
| Flash Point °C. | 204, min. |
| Viscosity at 98.9° C., mn$^{2/s}$ (SUs) | 4.2–7.4 (40–50) |
| Melting point range (°C.) | 46–68 |
| Refractive index at 98.9° C. | 1.430–1.433 |
| Average molecualr weight | 350–420 |
| Carbon atoms per molecule | 20–36 |

Polyethylene waxes are low molecular weight polyethylenes having wax-like properties. Such polyethylenes can be made by known techniques such as, for example, by high pressure polymerization, low pressure (Zeigler-type catalyst) polymerization, or controlled thermal degradation of high molecular weight polyethylene. Polymethylene waxes, also known in the art as Fischer-Tropsch waxes, are produced by polymerizing carbon monoxide under high pressure and over iron catalysts. Low molecular weight synthetic waxes and wax byproducts melting between about 100° and 160° F. are contemplated as useful in this invention.

The amount of saturated hydrocarbon wax included in the water dispersible compositions of the present invention generally will range from about 0.04 to about 10% by weight of the wax based on the total weight of the composition. When the composition is mixed with water to form the water-repellent aqueous systems of the present invention, the aqueous system should contain sufficient hydrocarbon wax to provide the desired water-repellent properties. Generally, the aqueous water-repellent systems of the present invention will contain from about 0.01 to about 5% by weight of the hydrocarbon wax, and more generally, up to about 2%. Mixtures of the hydrocarbon waxes can be utilized.

The water dispersible compositions (and aqueous systems) utilized in the present invention also contain (b) at least one oil-soluble metal salt. The oil-solubility of the metal salts of the invention is believed to contribute greatly to the advantageous and desirable results which are obtained. Since the organic compound is oil-soluble and essentially hydrophobic, it therefore, does not have a tendency to be extracted or leached from the treated wood even over an extended period of time.

Particularly preferred types of oil-soluble metal salts which are useful in the aqueous systems of the present invention are the acid, neutral and basic salts of organic carboxylic acids. These salts also are known in the art as "soaps".

The choice of metal contained in the salts will depend upon the properties which are desired to be imparted to the wood being treated, availability, cost and effectiveness. Certain metals are more commonly used in the method of the invention, and these include, copper, zinc, zirconium, chromium, iron, antimony, lead and mercury. Salts containing a mixture of the ions of two or more of these metals also can be used.

As mentioned, the salts can be acid, neutral or basic. The acid salts contain insufficient metal cation to neutralize the acid. The neutral salts contain an amount of metal cation just sufficient to neutralize the acidic groups present in the salt anion. The basic salts contain an excess of metal cation and are often referred to as overbased, hyperbased or superbased salts. These acid, basic and neutral salts preferably are of oil-soluble organic carboxylic acids and mixtures of such acids.

The carboxylic acids from which suitable acid, neutral and basic salts can be prepared include aliphatic, cycloaliphatic and aromatic mono- and polybasic carboxylic acids. The organic carboxylic acids can be either natural or synthetic or mixtures thereof. The examples of natural acids, although usually refined, include straight and branched chain carboxylic acids and mixtures such as tall oil acids and cyclic carboxylic acids such as naphthenic acids. A variety of synthetic carboxylic acids, and particularly aliphatic carboxylic acids or mixtures thereof is useful, and these generally contain six or more carbon atoms.

The metal salts or soaps can be prepared by fusion or precipitation methods. The soaps normally are prepared in an inert liquid medium such as a hydrocarbon oil or solvent. The organic carboxylic acids generally will have at least six carbon atoms and as many as 30 carbon atoms, but when more than one carboxylic acid is employed, carboxylic acids containing as little as two carbon atoms may be employed as one of the acids of the mixture. Examples of useful organic carboxylic acids include acetic acid, propionic acid, butyric acid, isopentanoic acid, hexoic acid, 2-ethyl butyric acid, nonylic acid, decanoic acid, 2-ethylhexoic acid, isooctanoic acid, isononanoic acid, neodecanoic acid, lauric acid, palmitic acid, stearic acid, oleic acid, linolic acid, naphthenic acid, and commercially available mixtures of two or more carboxylic acids such as naphthenic, tall oil acids, rosin acids, etc.

Examples of acid salts are acid copper salts containing less than a stoichiometric equivalent of copper per acid equivalent. For metals other than copper, the basic salts or soaps are preferred since these contain higher amounts of metal. For example, solutions of normal size zinc salts of monocarboxylic acids such as neodecanoic acid contain about 6% zinc by weight whereas a solution of a basic zinc neodecanoate can contain up to about 16% by weight or more of zinc.

Basic metal salts or soaps of carboxylic acids also can be prepared by methods well known in the art. Examples of neutral and basic salts and of metal salt complexes as well as their preparation can be found in, for example, U.S. Pat. Nos. 2,251,798; 2,955,949; 3,723,152 and 3,941,606 which disclosures are hereby incorporated by reference. Some of the basic salts have been referred to as complexes because they are not simple salts. For example, the basic compositions described in U.S. Pat. No. 3,941,606 are referred to as "metal carboxylate-alkoxy alcoholate" complexes. For the purpose of this invention such basic complexes are to be included in the term metal salts or soaps as used in this specification and claims.

Specific examples of the salts or soaps which are useful in the invention include those described below in Table III and the following specific examples.

TABLE II

| | Carboxylate Metal Salts | | |
| --- | --- | --- | --- |
| Component | Metal | Metal Content (wt. %) | Acid |
| B-1 | Cu | 16 | neodecanoic |
| B-2 | Cu | 11 | neodecanoic |
| B-3 | Cu | 6 | naphthenic |
| B-4 | Zn | 18 | 2-ethyl hexoic |
| B-5 | Zn | 8 | naphthenic |
| B-6 | Zn | 10 | mixture of $C_8$–$C_{13}$ |

The preparation of the above-described metal salts is illustrated by the following examples wherein all parts and percentages are by weight unless otherwise stated.

EXAMPLE B-1

A mixture of 260 parts of crude neodecanoic acid, 103 parts of propionic acid, 400 parts of mineral spirits, 172 parts of copper powder, 91 parts of Methyl Cellosolve, 14 parts of dipropylene glycol, 70 parts of water, 10 parts of octyl-phenoxy polyethoxy ethanol (Triton X-15 from Rohm & Haas Company) and 3 parts of Santoflex-77 is prepared and sparged with air while heating to a temperature of about 80° C. Reaction under these conditions continues for about 6 hours. A small amount of boric acid (7 parts) is added and the heating is continued at 80° C. with air sparging. The reaction is continued at this temperature until 180% acid neutralization is achieved (total, 14 hours). The mixture is heated for an additional 2 hours at a temperature of about 150° C. to 190% acid neutralization. The air blowing is terminated, and an inert nitrogen atmosphere is employed while the mixture is slowly heated to about 150° C. over a period of 8 hours while excess water is removed.

Four approximately equal proportions of amyl phosphate totalling 176 parts are added at 3-hour intervals while maintaining a temperature of about 145° C. and a nitrogen atmosphere. The mixture then is cooled to about 125° C., settled to remove excess copper and filtered.

The filtered product can be heated under vacuum to a temperature of about 150° C. in order to remove the mineral spirits to yield the desired concentration of metal.

The compositions of Examples B-2 through B-6 in Table I can be prepared by methods similar to those described above for B-1 or by alternative procedures known in the art.

EXAMPLE B-7

A mixture of 840 parts of distilled naphthenic acid, 176 parts of 2-ethyl hexoic acid, 512 parts of mineral spirits, 48 parts of Carbitol (a diethylene glycol ether available commercially from Union Carbide Corp.), 4.8 parts of acetic acid, 1.6 parts of water and 10.9 parts of an anti-foam agent is charged to a reactor, and the mixture is heated with agitation to a temperature of about 65° C. The mixture is sparged with carbon dioxide and 214.4 parts of zinc oxide are added to the mixture which is then heated to a temperature of about 105° C. The reaction is continued at this temperature while periodic checks are made for percent zinc, the acid value and percent water. If necessary, the acid value is adjusted to minus 33 to minus 38 for 10% zinc. If the water content is over 0.4%, the mixture is dehydrated.

About 100 parts of filter acid are added with stirring to the mixture which is then filtered. The filtrate is a clear liquid which is adjusted to a zinc content of 10% using mineral spirits to form the desired product.

Carboxylate metal salts of the type described above are available commercially such as from Mooney Chemicals, Inc., Cleveland, Ohio, 44113 under the general trade designations TEN-CEM, CEM-ALL, NAP-ALL, HEX-CEM, LIN-ALL, and NEO-NAP. These mineral spirit solutions can be adapted for use in preparing the water dispersible compositions and aqueous systems of the present invention by adjusting the mineral spirits content (generally reducing the amount of mineral spirits) and mixing said mineral spirit solutions with water and surfactants as described below.

Water dispersible solutions/dispersions of metal salts also are available from Mooney Chemicals, Inc. under the general trade designation M-GARD(TM). The metal content of these salts also ranges from about 4% to about 10% by weight, but these solutions/dispersions already contain the desired surfactants and can be readily mixed with water and wax to form the desired aqueous systems. Mixtures of the carboxylic acid salts such as those described in Table I are easily prepared and utilized in accordance with the invention. For example, a mixture in accordance with the invention is prepared from equal parts of components B-1 and B-6 resulting in a mixture containing 8% copper and 5% zinc. A mixture of two parts of component B-1 with one part of component B-6 will contain 10.7% copper and 3.3% of zinc.

Examples of other neutral and basic salts include lead naphthenate, lead neodecanoate, lead 2-ethyl hexoate, lead tallate, zinc tallate, chromium 2-ethyl hexoate, chromium tallate, chromium oleate, antimony octoate, antimony oleate, iron naphthenate, iron tallate, phenyl mercury oleate, mercury dioleate, etc.

The amount of the metal salt included in the water dispersible compositions of the invention may vary over a wide range. Generally, however, the amount of metal salt or salts contained in the water dispersible compositions will be an amount sufficient to provide a metal content of from about 1 to about 30% by weight of metal based on the weight of the composition.

In addition to the hydrocarbon wax and the metal salts and soaps described above, the water dispersible compositions of the invention also contain at least one surfactant. Preferably, the surfactants are anionic, nonionic or amphoteric surfactants. Many such surfactants are known in the art. See, for example, McCutcheon's "Emulsifiers and Detergents", 1984, North American Edition, published by McCutcheon's Division, MC Publishing Corporation, Glen Rock, N.J., U.S.A., particularly pages 311-317 which are hereby incorporated by reference for their disclosure in this regard.

In general, the nonionic surfactants such as those containing ether linkages are particularly useful. Examples of such ether-containing surfactants are those having the general formula

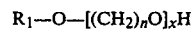

$$R_1-O-[(CH_2)_nO]_xH$$

wherein $R_1$ is an aryl or alkyl group containing from about 6 to 20 carbon atoms, n is two or three, and x is an integer between 2 and 100. Such surfactants are produced generally by treating fatty alcohols or alkyl-substituted phenols with excess ethylene oxide or propylene oxide. The alkyl carbon chain may contain from about 6 to 20 carbon atoms and may be derived from a long chain fatty alcohol such as oleyl alcohol or stearyl alcohol.

Nonionic polyoxyethylene compounds of this type are described in U.S. Pat. No. 3,855,085. Such polyoxyethylene compounds are available commercially under the general trade designations "Surfynol" by Air Products and Chemicals, Inc. of Allentown, Pa., and under the designation "Pluronic" or "Tetronic" by BASF Wyandotte Corp. of Wyandotte, Mich. Examples of specific polyoxyethylene condensation products include "Surfynol 465" which is a product obtained by reacting about 10 moles of ethylene oxide with 1 mole of tetramethyldecynediol. "Surfynol 485" is the product obtained by reacting 30 moles of ethylene oxide with tetramethyldecynediol. "Pluronic L 35" is a product obtained by reacting 22 moles of ethylene oxide with polypropylene glycol obtained by the condensation of 16 moles of propylene oxide. Also useful are various polyoxyalkylene sorbitol derivatives obtained by reaction of sorbitol (or similar polyhydroxy compounds) with alkylene oxide such as ethylene oxide. These products may be used as obtained, or they may be further reacted with acids such as fatty acids to form esters or with ammonia or amino compounds to form ammonium or amine salts. Examples of commercially available materials of these types include Atlas G-1096 which is a polyoxyethylene (50) sorbitol hexaoleate; Atlas G-1087 which is a polyoxyethylene sorbitol polyoleate; Atlas G-1045A which is a polyoxyethylene sorbitol polyoleate-laurate; Atlox 1045A which is a polyoxyethylene sorbitol ester; etc. All of the above specified materials are available from ICI Americas, Inc.

Amine, long chain fatty amine, long chain fatty acid alkanol amines, diamines, amides, alkanol amides and polyglycol-type surfactants known in the art are also useful. One type found particularly useful is the group obtained by the addition of a mixture of propylene oxide and ethylene oxide to diamines. More specifically, compounds formed by the addition of propylene oxide to ethylene diamine followed by the addition of ethylene oxide are useful and are available commercially from BASF Wyandotte Inc. Chemical Group under the general trade designation "Tetronic".

Carbowax-type wetting agents which are polyethylene glycols having different molecular weights have been found to give good results. For example Carbowax No. 1000 has a molecular weight range of from about 950 to 1,050 and contains from 20 to 24 ethoxy units per molecule. Carbowax No. 4000 has a molecular weight range of from about 3000 to 3700 and contains from 68 to 85 ethoxy units per molecule. Other known nonionic glycol derivatives such as polyalkylene glycol ethers and methoxy polyethylene glycols which are available commercially can be utilized as surfactants in the water dispersible compositions of the invention.

Anionic surfactants also are useful in the aqueous systems of the invention. Among the useful anionic surfactants are the widely-known metal carboxylate soaps, organo sulfates, sulfonates, sulfocarboxylic acids and their salts, and phosphates. Various anionic surfactants are readily available commercially, and further information about anionic surfactants can be found in the text "Anionic Surfactants" Parts II and III, edited by W. M. Linfield, published by Marcel Dekker, Inc., New York, 1976. Examples of anionic surfactants available from ICI Americas, Inc. include Atlas G-2205 which is an aromatic phosphate and Atlas G-3300 which is an alkyl aryl sulfonate. Examples of anionic surfactants available from Rohm and Haas Company include Triton 770 which is a sodium salt of an alkyl aryl polyether sulfate, Triton GR-5M which is a dioctyl sodium sulfosuccinate, Triton H-55 which is a phosphate surfactant, potassium salt, Triton W-30 and Triton X-200 which are sodium salts of alkyl aryl polyether sulfonates, etc.

Mixtures of the nonionic surfactants can and are generally utilized in the water dispersible compositions and the aqueous systems of the present invention. The amount of surfactant contained in the water dispersible compositions of the invention can vary over a wide range but generally will be from about 3 to about 30% by weight. The amount of surfactant contained in the aqueous systems is generally from about 0.05% to about 10% by weight.

The water dispersible compositions of the present invention also contain (d) at least one hydrocarbon solvent. The amount of hydrocarbon solvent contained in the water dispersible composition can vary over a wide range. The water dispersible compositions may contain as much as 96% by weight of the hydrocarbon solvent although lesser amounts generally are used. Examples of hydrocarbon solvents useful in this invention include aromatic as well as aliphatic solvents and mixtures of aromatic and aliphatic hydrocarbons. Specific examples of hydrocarbon solvents include mineral spirits, naphtha, light mineral oil, xylene, toluene, etc.

The aqueous systems of the present invention can be prepared by mixing the wax, metal salt, the surfactants and hydrocarbon solvents with sufficient water to provide the desired levels of ingredients. The amount of water can vary over a wide range, but generally the aqueous system will contain from about 25 to 99% by weight of water. The aqueous systems also can be prepared from the water-dispersible compositions described above which contain the wax, the metal salt(s), one or more surfactants and a hydrocarbon solvent. As mentioned above, such water dispersible compositions, without the wax, are available commercially such as from Mooney Chemicals, Inc. under the general trade designation M-GARD. Moreover, such water-dispersible additive concentrates can be prepared by adding the wax (melted) to commercially available solutions of metal salts and mineral spirits or by blending the mineral spirit solutions with the wax (melted) and desired surfactants with or without additional hydrocarbon solvents such as mineral oils. For example, a water-dispersible composition can be prepared from the metal salt solutions in mineral spirits illustrated above as Examples B-1 to B-7 by thoroughly mixing the mineral spirit solutions with mineral oil, melted paraffin wax and surfactants. A specific example of such a procedure is the blending of 770 parts of the product of Example B-7 with 100 parts of mineral oil, 30 parts of paraffin wax, 75 parts of Atlas G-3300 and 25 parts of Atlox-1045A. Similar water-dispersible compositions useful in preparing the aqueous systems of the invention can be prepared from compositions identified as B-1 to B-7 utilizing the same or other wax and surfactants.

Water-dispersible compositions of the type described above are desirable in that they can be readily shipped to the point of use whereupon a desirable amount of water is added and mixed. Not only is the cost of shipping reduced, but also the end formulation to an extent can be tailored depending upon the particular application, type of substrate to be treated, or the like.

The water-dispersible compositions of the types described above can be converted to the aqueous system of the invention by dilution with water. The dilution is accomplished by standard mixing techniques.

The water-dispersible compositions and the aqueous systems of the present invention also may contain other additives which impart desirable properties to the treated substrates. For example, the aqueous systems of the invention may contain (f) flame retardant compositions, (g) coloring agents, (h) insecticides and (i) odorants, (j) moldicides, (k) wood stabilizing agents, etc. When included in the water-dispersible compositions, such additives may be present in amounts ranging from about 0.01 to about 20–30%. The amount of such additives included in the aqueous systems of the invention may vary over a rather wide range although amounts of from about 0.01 to about 5% of these compositions generally are satisfactory.

Inorganic fire retardant compositions are particularly useful in the aqueous systems of the invention. Examples of inorganic materials include metal oxides which are well known in the art such as antimony oxide, etc. Examples of organic fire retardants include a number of halogenated and organophosphorus compounds which may be dispersed in the aqueous systems.

Although the various substrates such as wood which can be treated in accordance with the method of the invention may have a satisfactory appearance for most purposes, the appearance can be modified if desired by imparting different color effects. The present invention contemplates the inclusion in the aqueous systems of coloring agents which either are soluble or dispersible in the aqueous systems of the invention. Any of the known oil-soluble or water dispersible coloring agents can be used. These agents are mixed either with the water dispersible additive concentrates of metal salts described above, or the aqueous systems, and when the wood is immersed in the aqueous systems of the invention containing coloring agents, the coloring agents penetrate the wood with the metal salts give desirable coloring effects which in many instances emphasize the grain of the wood. Examples of coloring agents which may be used depending on the desired results include: Bruco Creosote Brown RGY available from Bruce Chemical Co., Iron Cem-All available from Mooney Chemical Inc., and Pylaklor Red Brown LX-6249 available from Pylam Dye Co.

Insecticides also can be included in the aqueous systems of the invention, and it is preferable that the insecticide either be soluble in oil, water or readily dispersible in water. Examples of such insecticides include Dursban TC available from Dow Chemical and Ficam 76WP available from BFC Chemicals Inc.

Odorants can be included in the water dispersible compositions and in the aqueous systems of the invention, and one preferred odorant is pine oil. Other water-soluble or dispersible compounds having desired odors can be included in the aqueous systems.

Wood stabilizing agents are included in the water-dispersible and aqueous systems of the invention to provide the wood treated with the aqueous systems with improved dimensional stability. Such agents remain in the cell walls when the wood is dried, and this bulking action prevents the wood from shrinking. Various chemicals have been suggested for this purpose in the art of wood treating. A useful group of stabilizing agents are the polyalkylene glycols, and more particularly, the polyethylene glycols. The molecular weight of the glycols should be selected so that the glycols are soluble in water. Thus, polyethylene glycols having molecular weights of up to about 6000 are desirable because these generally are water soluble. Various of these polyethylene glycols are available commercially.

The aqueous water-repellent systems of the present invention preferably have fungicidal properties and comprise:
(a) from about 0.02 to about 5% by weight of a paraffinic wax,
(b) a fungicidally effective amount of at least one oil-soluble metal salt of an organic carboxylic acid,
(c) from about 0.05 to about 10% by weight of at least one surfactant,
(d) up to about 30% by weight of at least one hydrocarbon solvent, and
(e) from about 25 to about 99% by weight of water.

The process of this invention involves contacting the substrate with the aqueous systems a period of time sufficient to enable the desired amount of paraffin wax and metal salt to penetrate into the substrate. Contact between the substrate and the aqueous system can be effected by brushing, spraying, painting, dipping, soaking, or immersion under vacuum or pressure, etc. Although the aqueous water repellent systems are useful in treating a variety of substrates, the invention will be described with respect to the treatment of wood. However, other substrates such as cloth, canvas, concrete, rope, etc. can be treated by the same or by slightly modified processes adapted to the particular substrate.

In one method of the present invention, the aqueous composition in which the wood is immersed can be maintained at a temperature of from about 5° to about 95° C. However, the method of the invention can be, and is preferably carried out at ambient temperature thereby eliminating the need for any equipment or materials for heating or cooling the aqueous systems. In some instances, it may be advantageous to heat the aqueous systems to elevated temperatures to increase the rate of penetration. In another embodiment, the wood to be treated can be heated to an elevated temperature, and the heated wood is then immersed in the aqueous system which has not been heated but is at room temperature or lower. The temperature differential causes a partial vacuum and results in improved penetration and rate of penetration.

As mentioned above, after the wood has been immersed in the aqueous systems of the present invention for the desired period of time, the wood is removed from the aqueous system. The thus treated wood is ready for shipping, although it may be desirable in some instances to allow the wood to at least partially dry before shipping.

The present invention surprisingly yields good water repellency even though the hydrocarbon wax is applied to the wood in an aqueous system. The aqueous systems of the invention are liquids that penetrate and continue to penetrate into wood over a period of time even when applied by non-pressure methods. Furthermore, the aqueous systems do not adversely affect the color of the wood, leave the surface of the wood free from objectionable contamination with oily, gummy or powdery ingredients of the water repellent, or in the case of a coating of appreciable thickness, leave the wood amenable to the application of paints, enamels, varnishes or other wood finishes commonly used on the wooden products for which the water repellent is offered.

It is surprising that desirable results can be obtained with such short contact times of the wood and aqueous systems. It is believed that the aqueous systems used in this invention deposit the desired amount of material on and in the outer layers of the wood during the brief contact to provide the desired results even though the paraffin wax, metal salts and other additives have not completed the penetration process into the wood. After the treated wood is removed from the aqueous system, the salts and other additives continue to penetrate into the wood while the wood is in storage or in shipment. Accordingly this invention provides a method for treating wood which not only uses inexpensive equipment (such as a large open tank), but a method by which the wood to be treated is in the equipment for short periods of time.

The method of the invention also can be conducted on wood contained in an enclosed vessel under vacuum or pressure conditions or a combination thereof. The use of pressure for improving the penetration of various chemicals into all types of wood is well known in the art. In this technique, the green wood is placed in a chamber which is sealed, heated and evacuated in a regulated cycle. Generally, the heating period varies from about 1 to 20 hours when steam is used as the source of heat. The evacuation step will vary from about 15 minutes to 2 hours, and the pressure within the sealed chamber is brought to level from zero to about thirty inches of mercury. The purpose of this step is to remove air and volatiles from the wood. The diluted aqueous systems of the invention then are introduced into the enclosed container, and the amount of water dispersible composition should be sufficient to immerse the wood completely. Pressurization of the vessel is then initiated and the pressure maintained at a desired level for a given period of time. Initially, the pressure within the vessel will decrease as the aqueous system within the container penetrates into the wood. The pressure is maintained at a desirable level throughout the penetration period of treatment by adding more of the aqueous system. When there is no longer any penetration of the liquid into the wood, the pressure can be released, the vessel drained, and the wood removed.

The details of the pressure process, including pressure ranges, concentration of aqueous composition and the cycling of vacuum and pressure with respect to a particular species of wood can be readily determined by one skilled in the art from the examples which follow and also by following the procedure of this invention on the particular wood while varying process parameters to provide optimum results. For example, the pressures utilized in the above-described pressure method can be as high as 300 psig., and are generally from about 50 to 200 psig.

The method of the invention can be carried out on a wide variety of wood types. The actual time of contact of the wood with the aqueous systems of the invention will vary depending on a variety of factors such as, for example, (1) whether the immersion of the wood is at atmospheric pressure or at elevated pressures as described above, (2) the amount of metal salt and insecticide to be introduced into the wood, (3) the difficulty of penetration into the particular type of wood being treated and (4) whether the wood is green wood or seasoned wood. Any type of wood, dry or green, can be treated with the water dispersible compositions of the invention. Green wood generally is defined as wood containing 30% or more by weight of water. Dry wood is defined as wood containing less than 30% by weight of water based on bone dry wood. Examples of wood species which can be treated in accordance with the method of the invention include Southern Yellow Pine, Western Red Cedar, Douglas Fir, Inland Fir, Spruce, Hemlock, Sugar Maple, Ash, Walnut, Cherry, White Pine, Red Pine, Birch, Red Oak, White Oak, Elm, Hickory, Linden, Beech, Sycamore, etc.

The invention will better be understood by reference to the following examples of water-dispersible compositions.

EXAMPLE I (WATER-DISPERSIBLE COMPOSITION)

|  | wt. % |
|---|---|
| Paraffin wax (mp 107° F.) | 4 |
| Zinc Nap-All (8% Zinc) | 74 |
| Atlas G-1096 (anionic surfactant) | 12 |
| Mineral spirits | 10 |

EXAMPLE II

| Paraffin Wax (mp 120° F.) | 3 |
|---|---|
| Product of Example B-7 (10% Zinc) | 80 |
| Atlas G-1096 (nonionic) | 10 |
| Atlas G-3300 (anionic) | 2 |
| Mineral spirits | 5 |

EXAMPLE III

| Paraffin Wax (mp 122° F.) | 2 |
|---|---|
| Zinc Nap-All (8% Zinc) | 74 |
| Atlox 1045A (anionic) | 10 |
| Hisol 10 | 5 |
| Mineral spirits | 9 |

EXAMPLE IV

| Paraffin Wax (mp 130–132° F.) | 2 |
|---|---|
| Zinc Nap-All (8% Zinc) | 80 |
| Atlas G-1096 (nonionic) | 10 |
| Atlas G-3300 (anionic) | 2 |
| Pine oil | 1 |
| Hisol 10 | 2.5 |
| 510 Oil | 2.5 |

EXAMPLE V

| Paraffin Wax (mp 130–132° F.) | 1–4 |
|---|---|
| Product of Example B-7 | 75 |
| Atlas G-1096 | 7.5 |
| Atlas G-3300 | 1.4 |
| Atlox 1045A | 0.5 |
| Pine oil | 1 |
| 510 Oil | 10 |
| Hisol 10 | remainder |

In preparing the water-dispersible compositions of the type illustrated in the above examples, it is preferred that the metal salt-mineral spirits solution be heated to a temperature of about 150°–180° F., and the melted wax is added with stirring. Pine oil then is added if desired followed by the hydrocarbon solvents and the surfactants. The temperature of the mixture, as well as any component added to the mixture, is preferably above the melting point of the wax component. The mixture is stirred until homogeneous.

As mentioned above, the aqueous water repellent systems of the present invention can be prepared from the various components or can be prepared by blending the above described water-dispersible compositions with sufficient water to provide the aqueous systems containing the desired amounts of the various ingredients. The water-dispersible compositions can be blended with water by any blending technique known to those skilled in the art.

The following Example illustrates the process of the invention conducted at atmospheric pressure in an open tank.

EXAMPLE A

Logs (debarked) are immersed in an aqueous system prepared by diluting one part of the composition of Example IV with 3 parts of water. The aqueous system is maintained at ambient temperature, and the wood logs are immersed in the aqueous system for about 6 minutes. The logs then are removed from the aqueous system and allowed to drip dry. Examination of the log specimens treated in accordance with this procedure shows good water repellency, zinc pick-up and retention. Moreover, subsequent examination of the log specimens treated in accordance with this procedure shows excellent penetration of the zinc salt into the logs, and there is no significant change in the original dimensions and surface texture of the wood. The metal salts which have penetrated into the wood logs exhibit resistance to leaching by water.

The following is a specific example of the method of the invention conducted at elevated pressures in an enclosed vessel.

EXAMPLE B

Norway pine logs are pressure treated with an aqueous system prepared by diluting one part of the composition of Example IV with 3 parts of water. The logs are immersed in the system in an enclosed pressure vessel. The pressure treatment is conducted at a maximum pressure of 200 psig for a total pressure time of about one hour. The logs are then removed from the vessel and allowed to drip dry. The logs treated in this manner exhibit good water repellency and the logs contain zinc which exhibits good retention properties.

The utility of the aqueous systems of the present invention to impart water repellent properties to wood is demonstrated by subjecting treated wood specimens to the "NWMA M-2 Swellometer Test". This test is designed to measure the effectiveness of water-repellent preservative formulations for retarding dimensional changes in wood submerged in water. By use of this test method, it can be determined if a commercial water-repellent preservative formulation meets the water-repellent requirements of the National Woodwork Manufacturers Association. The wood used in these tests must be straight-grain, flat-sawn, clear, kiln-dried Ponderosa pine sapwood. The boards are cut in a manner to give specimens ¼ inch in a longitudinal dimension, 1.5 inches in the radial dimension, and 10 inches in the tangential dimension. The swelling of an untreated specimen from each parent board is determined before the test.

Two adjacent specimens from five different boards (10 specimens in all) make up one set for testing the water-repellency of one formulation. The formulation to be tested is maintained at a temperature of about 21° C. Five of the test specimens (one from each board) are fully immersed in the formulation to be tested. The immersion time is three minutes. Both the treated and untreated specimens are placed separately on a raised screen or other suitable rack in a conditioning room or chamber until the specimens reach a constant weight.

The water-repellency of the treated wood specimens is tested by comparing the swelling of the untreated control with the swelling of the treated specimen after each has been submerged in distilled water. The swelling is measured by means of Swellometer instrument. A specimen is inserted in the guides of the Swellometer, placed so that one end bears firmly on the adjusted base and the other end contacts the plunger of the dial. A reading of the dial is made before immersion in water. The treated wood samples are then totally submerged in the water, and at the end of a 30-minute period, a second dial reading is taken and the difference is noted. The procedure is repeated for each of the five untreated controls and matching five treated samples using fresh distilled water each time. The difference between the swelling of the treated specimen and the swelling of the matching untreated control specimen is divided by the swelling of the untreated control specimen and multiplied by one hundred. The average of the five percentages (five specimens) represents the percent effectiveness of the water-repellent formulation. If the average effectiveness of the various formulations is 60% or more, the formulation shall be considered to have passed the test.

The results observed when the NWMA Swellometer Test is conducted on wood specimens treated in accordance with the present invention with aqueous systems prepared from the water-dispersible composition of Example V diluted with water to provide the desired concentration of components, and particularly of percent zinc and percent wax are summarized in the following Table.

| Aqueous System | | | |
|---|---|---|---|
| Example | % Zinc | % Wax | % Water Repellency |
| Control-1 | 0 | 0 | 0 |
| Control-2 | 3.0 | 0 | 52 |

-continued

| Aqueous System | | | |
|---|---|---|---|
| Example | % Zinc | % Wax | % Water Repellency |
| Va | 3.0 | 0.5 | 81 |
| Vb | 3.0 | 1.0 | 86 |
| Vc | 3.0 | 2.0 | 90 |
| Vd | 1.5 | 0.5 | 80 |
| Ve | 2.0 | 0.5 | 76 |

As apparent from the above results, small amounts of paraffin wax yielded significant increases in water repellency. In particular, when an amount of 0.5%, 1% or 2% paraffin wax is utilized, values of 81, 86, and 90% are obtained as compared to 52% with the control containing no paraffin wax.

The utility of the aqueous systems on wood is demonstrated also by the following test. A southern yellow pine sapwood board (1"×8"×4') was brush treated with the aqueous system described above as V(c) on all sides. After standing six days the treated board and a similar untreated board were set outside in the rain in a flat position for five hours. The average rain for the local area was recorded at 1.5 inches during this period. The boards were weighed before and after the rain, and the results are shown in the following table.

| | Outdoor Swelling Test | | | |
|---|---|---|---|---|
| | Weight (grams) of Boards | | Gain | |
| | Before Rain | After Rain | (g) | (%) |
| Untreated | 1290 | 2079 | 789 | 61.1 |
| Treated | 1756 | 1899 | 143 | 8.1 |

The reduction in weight of water absorbed is quite significant and represents a water repellency of 82%. Water repellency is measured as follows:

$$W.R. = \frac{(\text{weight untreated}) - (\text{weight treated})}{\text{weight untreated}} \times 100$$

In accordance with the patent statutes, while preferred embodiments and best mode have been described in detail, the scope of the invention is not limited thereto, but rather by the scope of the attached claims.

I claim:

1. A water dispersible composition useful in preparing aqueous water repellent compositions comprising
   (a) from about 0.04 to about 10% by weight of at least one saturated hydrocarbon wax,
   (b) at least one metal salt of an organic carboxylic acid in an amount sufficient to provide a metal content in the composition of from about 1 to about 30% by weight,
   (c) from about 3 to about 30% by weight of at least one surfactant, and
   (d) up to about 96% by weight of at least one hydrocarbon solvent.

2. The water dispersible composition according to claim 1, also containing at least one odorant, insecticide, flame retardant, wood stabilizing agent, or mixture thereof.

3. The water-dispersible composition of claim 1 also containing at least one moldicide.

4. The water dispersible composition according to claim 1, wherein the metal of the metal salt is at least one of zinc, copper, chromium, zirconium, iron, antimony, lead or mercury.

5. The water dispersible composition according to claim 4, wherein the metal is zinc or copper or a mixture thereof.

6. The water dispersible composition according to claim 1, wherein the hydrocarbon wax contains from about 18 to about 40 carbon atoms.

7. The water dispersible composition according to claim 1, wherein the carboxylic acid is at least one aliphatic or alicyclic monocarboxylic acid containing from about 6 to about 30 carbon atoms.

8. The water dispersible composition according to claim 1, also containing at least one odorant or insecticide or mixture thereof.

9. The water-dispersible composition of claim 1 wherein the hydrocarbon wax is characterized as having a melting point of between about 100° to about 160° F.

10. An aqueous water repellent system having fungicidal properties comprising
    (a) from about 0.01 to about 5% by weight of a paraffinic wax,
    (b) a fungicidally effective amount of at least one one oil-soluble metal salt of an organic carboxylic acid,
    (c) from about 0.05 to about 10% by weight of at least one surfactant,
    (d) up to about 30% by weight of at least one hydrocarbon solvent, and
    (e) from about 25 to about 99% by weight of water.

11. A water repellent system according to claim 10, including an insecticide, odorant, flame retardant, or mixture thereof.

12. A water repellent system in accordance with claim 10, wherein the metal salt is present in an amount sufficient to provide a metal content in the aqueous mixture of from about 0.05 to about 5% by weight.

13. A water repellent system according to claim 10, wherein the metal of the metal salt is selected from the group consisting of zinc, copper, chromium, iron, zirconium, antimony, lead, mercury, or combinations thereof.

14. A water repellent system according to claim 10, wherein said wax is a mixture of hydrocarbons containing from about 18 to about 40 carbon atoms.

15. A water repellent system according to claim 14, wherein the acid is at least one aliphatic or alicyclic monocarboxylic acid containing from about 6 to about 30 carbon atoms.

16. A water repellent system in accordance with claim 10, wherein the salt of (c) is a zinc or copper salt of at least one aliphatic or alicyclic monocarboxylic acid containing from about 6 to 30 carbon atoms, or mixtures thereof.

17. A water repellent system in accordance with claim 16, wherein the monocarboxylic acids contain from about 6 to 24 carbon atoms.

18. A method of imparting water repellency and fungicidal properties to permeable substrates comprising the steps of:
    (a) contacting the substrate with the aqueous system of claim 10 for a period of time sufficient to enable the metal salt to penetrate into the substrate, and
    (b) removing said substrate from contact with said aqueous mixture.

19. The method of claim 18 wherein the substrate is wood.

20. The method of claim 18, wherein the metal content in the aqueous mixture is from about 0.05 to about 5% by weight, said wax is a paraffinic wax and the amount of said wax is from about 0.1% to about 5% by weight.

21. The method of claim 18, wherein the acid is at least one aliphatic or alicyclic monocarboxylic acid containing from about 6 to about 30 carbon atoms.

22. The method of claim 19, including immersing said wood in the aqueous system maintained at a temperature of between about 5° C. and 95° C.

23. The method of claim 19, wherein the wood is immersed in the aqueous system and maintained in the system under fluid pressure in an enclosed pressure vessel.

24. The method of claim 19, wherein the aqueous system also contains at least one flame retardant, odorant, insecticide, moldicide, wood stabilizing agent, or mixtures thereof.

25. Wood treated in accordance with the method of claim 19.

26. The water-repellent system of claim 10 wherein the paraffinic wax is characterized as having a melting point of between about 100° to about 160° F.

27. The water-repellent system of claim 26 wherein the melting point of the paraffinic wax is between about 100° to about 140° F.

28. The water-repellent system of claim 10 also containing at least one flame-retardant, odorant, insecticide, moldicide, wood stabilizing agent, or mixtures thereof.

* * * * *